United States Patent
Miyazaki

(10) Patent No.: US 12,268,729 B2
(45) Date of Patent: Apr. 8, 2025

(54) THERAPEUTIC AGENT FOR NEURODEGENERATIVE DISEASE

(71) Applicant: Toru Miyazaki, Tokyo (JP)

(72) Inventor: Toru Miyazaki, Tokyo (JP)

( * ) Notice: Subject to any disclaimer, the term of this patent is extended or adjusted under 35 U.S.C. 154(b) by 883 days.

(21) Appl. No.: 17/280,157

(22) PCT Filed: Sep. 30, 2019

(86) PCT No.: PCT/JP2019/038530
§ 371 (c)(1),
(2) Date: Mar. 25, 2021

(87) PCT Pub. No.: WO2020/071318
PCT Pub. Date: Apr. 9, 2020

(65) Prior Publication Data
US 2022/0000975 A1   Jan. 6, 2022

(30) Foreign Application Priority Data

Oct. 1, 2018   (JP) .................................. 2018-186759

(51) Int. Cl.
| | |
|---|---|
| *A61K 38/17* | (2006.01) |
| *A61K 35/76* | (2015.01) |
| *A61K 35/761* | (2015.01) |
| *A61K 48/00* | (2006.01) |
| *A61P 25/28* | (2006.01) |

(52) U.S. Cl.
CPC .......... *A61K 38/1761* (2013.01); *A61K 35/76* (2013.01); *A61K 35/761* (2013.01); *A61P 25/28* (2018.01); *A61K 48/00* (2013.01)

(58) Field of Classification Search
None
See application file for complete search history.

(56) References Cited

U.S. PATENT DOCUMENTS

| | | |
|---|---|---|
| 2010/0028357 A1 | 2/2010 | Matsubara et al. |
| 2010/0331244 A1 | 12/2010 | Miyazaki |
| 2012/0009180 A1 | 1/2012 | Kubota et al. |
| 2015/0094268 A1 * | 4/2015 | Miyazaki .................. A61P 1/16 530/380 |
| 2017/0172120 A1 | 6/2017 | Miyazaki |
| 2018/0078539 A1 | 3/2018 | Habash |

FOREIGN PATENT DOCUMENTS

| | | |
|---|---|---|
| EP | 2573192 A1 | 3/2013 |
| JP | 5692073 B2 | 2/2015 |
| JP | 5765857 B2 | 8/2015 |
| WO | WO 2000/024392 A1 | 5/2000 |
| WO | WO 2010/140531 A1 | 12/2010 |
| WO | WO 2011/145725 A1 | 11/2011 |
| WO | WO 2013/162021 A1 | 10/2013 |
| WO | WO 2015/119253 A1 | 8/2015 |
| WO | WO-2018189661 A2 * | 10/2018 ............. A61K 35/16 |

OTHER PUBLICATIONS

Kurokawa et al. (Proc Natl Acad Sci U S A. Jul. 19, 2011;108(29):12072-7) (Year: 2011).*
Cleveland Clinic (downloaded on Mar. 4, 2024 from URL:<Neurodegenerative Diseases: What They Are & Types (clevelandclinic.org)>) (Year: 2024).*
National Institute of Aging (downloaded on Jul. 1, 2024 from URL:<https://www.nia.nih.gov/health/alzheimers-treatment/how-alzheimers-disease-treated#:~:text=Most%20FDA-approved%20drugs%20work,interventions%20that%20will%20cure%20Alzheimer%27s.>) (Year: 2024).*
National Health Service (downloaded on Jul. 1, 2024 from URL:<https://www.nhs.uk/conditions/parkinsons-disease/treatment/#:~:text=There%27s%20currently%20no%20cure%20for,medication>) (Year: 2024).*
Lykken et al., "Recent Progress and Considerations for AAV Gene Therapies Targeting the Central Nervous System," *J. Neurodev. Disord.*, 10(1): 16 (2018).
Miyazaki et al., "AIMing at Metabolic Syndrome—Towards the Development of Novel Therapies for Metabolic Diseases via Apoptosis Inhibitor of Macrophage (AIM)," *Circ. J.*, 75(11): 2522-2531 (2011).
European Patent Office, Extended European Search Report in European Patent Application No. 19869231.1 (Jul. 15, 2022).
Arai et al., "Apoptosis inhibitor of macrophage protein enhances intraluminal debris clearance and ameliorates acute kidney injury in mice," *Nat. Med.*, 22(2): 183-193 (2016).
Kurokawa et al., "Macrophage-Derived AIM Is Endocytosed into Adipocytes and Decreases Lipid Droplets via Inhibition of Fatty Acid Synthase Activity," *Cell Metab.*, 11(6): 479-492 (2010).
Kurokawa et al., "Apoptosis inhibitor of macrophage (AIM) is required for obesity-associated recruitment of inflammatory macrophages into adipose tissue," *Proc. Natl. Acad. Sci. U.S.A.*, 108(29): 12072-12077 (2011).
Miyazaki et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily," *J. Exp. Med.*, 189(2): 413-422 (1999).
Miyazaki, "Apoptosis Inhibitor of Macrophage," *Doctor Salon Library*, 58: 33-37 (2014).
Wang et al., "CD5L/AIM Regulates Lipid Biosynthesis and Restrains Th17 Cell Pathogenicity," *Cell*, 163(6): 1413-1427 (2015).
Japanese Patent Office, International Search Report in International Patent Application No. PCT/JP2019/038530 (Dec. 24, 2019).

* cited by examiner

*Primary Examiner* — Sergio Coffa
(74) *Attorney, Agent, or Firm* — Leydig, Voit & Mayer, Ltd.

(57) ABSTRACT

The present invention provides an agent for the treatment or prophylaxis of a neurodegenerative disease, containing an apoptosis inhibitor of macrophage (AIM), an AIM fragment having a biological activity of AIM, or a nucleic acid encoding the AIM or AIM fragment.

10 Claims, 7 Drawing Sheets
Specification includes a Sequence Listing.

SEQUENCE LISTING

```
<160> NUMBER OF SEQ ID NOS: 6

<210> SEQ ID NO 1
<211> LENGTH: 347
<212> TYPE: PRT
<213> ORGANISM: Homo sapiens

<400> SEQUENCE: 1

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
                20                  25                  30

Cys Glu Gly Arg Val Glu Val Glu Gln Lys Gly Gln Trp Gly Thr Val
            35                  40                  45

Cys Asp Asp Gly Trp Asp Ile Lys Asp Val Ala Val Leu Cys Arg Glu
        50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
```

```
                260                 265                 270
Trp Gly Glu Lys Glu Asp Gln Val Val Cys Lys Gln Leu Gly Cys Gly
            275                 280                 285

Lys Ser Leu Ser Pro Ser Phe Arg Asp Arg Lys Cys Tyr Gly Pro Gly
        290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
                340                 345

<210> SEQ ID NO 2
<211> LENGTH: 1044
<212> TYPE: DNA
<213> ORGANISM: Homo sapiens

<400> SEQUENCE: 2
atggctctgc tattctcctt gatccttgcc atttgcacca gacctggatt cctagcgtct      60
ccatctggag tgcggctggt ggggggcctc caccgctgtg aagggcgggt ggaggtggaa     120
cagaaaggcc agtggggcac cgtgtgtgat gacgcctggg acattaagga cgtggctgtg     180
ttgtgccggg agctgggctg tggagctgcc agcggaaccc ctagtggtat tttgtatgag     240
ccaccagcag aaaaagagca aaaggtcctc atccaatcag tcagttgcac aggaacagaa     300
gatacattgg ctcagtgtga gcaagaagaa gtttatgatt gttcacatga tgaagatgct     360
ggggcatcgt gtgagaaccc agagagctct ttctccccag tcccagaggg tgtcaggctg     420
gctgacggcc ctgggcattg caagggacgc gtggaagtga agcaccagaa ccagtggtat     480
accgtgtgcc agacaggctg gagcctccgg gccgcaaagg tggtgtgccg gcagctggga     540
tgtgggaggg ctgtactgac tcaaaaacgc tgcaacaagc atgcctatgg ccgaaaaccc     600
atctggctga gccagatgtc atgctcagga cgagaagcaa cccttcagga ttgcccttct     660
gggccttggg ggaagaacac ctgcaaccat gatgaagaca cgtgggtcga atgtgaagat     720 cccctttgact tgagactagt aggaggagac aacctctgct ctgggcgact ggaggtgctg     780
cacaagggcg tatggggctc tgtctgtgat gacaactggg gagaaaagga ggaccaggtg     840
gtatgcaagc aactgggctg tgggaagtcc ctctctccct ccttcagaga ccggaaatgc     900
tatggccctg ggttggccg catctggctg ataatgttc gttgctcagg ggaggagcag     960
tccctggagc agtgccagca cagattttgg gggtttcacg actgcaccca ccaggaagat    1020
gtggctgtca tctgctcagg atag                                          1044

<210> SEQ ID NO 3
<211> LENGTH: 42
<212> TYPE: PRT
<213> ORGANISM: Artificial Sequence
<220> FEATURE:
<223> OTHER INFORMATION: Synthetic Sequence - Amyloid beta 42

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 4
<211> LENGTH: 352
<212> TYPE: PRT
<213> ORGANISM: Mus musculus

<400> SEQUENCE: 4

Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
            20                  25                  30

Ala His Arg Cys Glu Gly Arg Val Glu Val Glu His Asn Gly Gln Trp
        35                  40                  45

Gly Thr Val Cys Asp Asp Gly Trp Asp Arg Arg Asp Val Ala Val Val
    50                  55                  60

Cys Arg Glu Leu Asn Cys Gly Ala Val Ile Gln Thr Pro Arg Gly Ala
65                  70                  75                  80

Ser Tyr Gln Pro Pro Ala Ser Gly Gln Arg Val Leu Ile Gln Gly Val
                85                  90                  95

Asp Cys Asn Gly Thr Glu Asp Thr Leu Ala Gln Cys Glu Leu Asn Tyr
            100                 105                 110

Asp Val Phe Asp Cys Ser His Glu Glu Asp Ala Gly Ala Gln Cys Glu
        115                 120                 125

Asn Pro Asp Ser Asp Leu Leu Phe Ile Pro Glu Asp Val Arg Leu Val
    130                 135                 140

Asp Gly Pro Gly His Cys Gln Gly Arg Val Glu Val Leu His Gln Ser
145                 150                 155                 160

Gln Trp Ser Thr Val Cys Lys Ala Gly Trp Asn Leu Gln Val Ser Lys
                165                 170                 175

Val Val Cys Arg Gln Leu Gly Cys Gly Arg Ala Leu Leu Thr Tyr Gly
            180                 185                 190

Ser Cys Asn Lys Asn Thr Gln Gly Lys Gly Pro Ile Trp Met Gly Lys
        195                 200                 205

Met Ser Cys Ser Gly Gln Glu Ala Asn Leu Arg Ser Cys Leu Leu Ser
    210                 215                 220

Arg Leu Glu Asn Asn Cys Thr His Gly Glu Asp Thr Trp Met Glu Cys
225                 230                 235                 240

Glu Asp Pro Phe Glu Leu Lys Leu Val Gly Asp Thr Pro Cys Ser
                245                 250                 255

Gly Arg Leu Glu Val Leu His Lys Gly Ser Trp Gly Ser Val Cys Asp
            260                 265                 270

Asp Asn Trp Gly Glu Lys Glu Asp Gln Val Val Cys Lys Gln Leu Gly
        275                 280                 285

Cys Gly Lys Ser Leu His Pro Ser Pro Lys Thr Arg Lys Ile Tyr Gly
    290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                325                 330                 335

Cys Thr His Lys Glu Asp Val Glu Val Ile Cys Thr Asp Phe Asp Val
            340                 345                 350

<210> SEQ ID NO 5
<211> LENGTH: 1059
<212> TYPE: DNA

<213> ORGANISM: Mus musculus

<400> SEQUENCE: 5

```
atggctccat tgttcaactt gatgctggcc atcttgagca ttttgttgg atcgtgtttt     60
tcagagtctc caaccaaagt gcagctagtg ggaggtgccc accgctgtga agggcgagtg    120
gaggtggaac acaatggcca gtgggggact gtgtgtgatg atggctggga ccggcgtgat    180
gtggctgtgg tgtgccgaga gctcaattgt ggagcagtca tccaaacccc gcgtggcgca    240
tcatatcagc caccagcatc agagcaaaga gttcttattc aaggggttga ctgcaacgga    300
acggaagaca cgttggctca atgtgagcta aattacgatg ttttgactg ctcacatgaa     360
gaagatgctg gggcacagtg tgagaaccca gacagtgacc tcctcttcat tccagaggat    420
gtgcgtctag tagatggccc ggggcactgc cagggtcgag tggaggtgct ccaccagtcc    480
cagtggagca ctgtgtgtaa agcaggctgg aacttacagg tctcaaaggt ggtgtgcagg    540
cagctcgggt gtgggcgggc attactgacc tacggaagct gcaacaagaa tactcagggc    600
aaaggaccca tctggatggg caagatgtcg tgttctggac aagaagcaaa ccttcggtct    660
tgccttttga gtcgtttgga gaacaactgt acccatggcg aggacacatg gatggaatgt    720
gaagatcctt tgagctgaa gctggtggga ggagacaccc cctgctctgg gaggttggag     780
gtgctgcaca agggttcctg gggctccgtc tgtgatgaca actggggaga aaaggaggac    840
caagtggtct gcaagcaact gggttgtggg aagtccctcc atccatcccc caaacccgg     900
aaaatctatg ggcctggggc aggccgcatc tggctggatg acgtcaactg ctcagggaag    960
gaacagtctc tggagttctg ccggcacagg ttgtgggggt accacgactg tacccacaag   1020
gaagatgtgg aggtgatctg cacagacttt gatgtgtga                          1059
```

<210> SEQ ID NO 6
<211> LENGTH: 1497
<212> TYPE: DNA
<213> ORGANISM: Artificial Sequence
<220> FEATURE:
<223> OTHER INFORMATION: Synthetic Sequence - Human PDGF-B promoter sequence (Xba I - Hind III)

<400> SEQUENCE: 6

```
tctagaggat ccacagtctc ctgagtagct gggactacag gagcttgtta ccacacccag     60
ctccagttta taaattcatc tccagtttat aaaggaggaa accgaggtac tgagaggtta    120
aaaaaccttc ctgcagacac ttgtccagca agtggccact ccaggatttg gaccaaggtg    180
atgtgtcttc aggctgtgtc tctgccactg tgccacgctg ctgggtggta ggcagcagtg    240
ggtgggtgcc tgcagtggtc tgtaaagacc acctgagatg tccttcctcc tctgttccac    300
cctgtccagg tccaagaaga cagtctatga agagagagca ggtgtgactc tctcagtgtg    360
ctcctctgtg agaagcaggc tgacatccca agggaaggg cggataacag agacagtgca     420
agcggaggag atgagggtgc ctcaaagccg ggaggctggg tgatgcagga gcctgcgtgt    480
cccgaggggg gtgctgggcc cagtgtgagt acgtgtgact gtgactgaga cagtgtgact    540
gctgaaggca gggacacagc agctccctga ctgggggcag aaggcgttaa ctgtgtgaag    600
gctggttgtg ggtgggtggg ctctgggcct cgaacccggg ggctgaggga gatagtaaac    660
agcagggtga ctgacgggaa gatcatgttg gtagccctgc gaagatgctg cagggctgtg    720
ggggtttgtg tgactttgca gttcaacaaa ttcaaattca gccaacgctg gcagggcctg    780
ttgtgccagg caaccagcta ggaggaggag actcggaccc agcttgcagc tgaagggcgc    840
```

```
tggctgccgg gttctgtggg ttcaccttgc ggtgtcttcc cttgctaaca ctgagtcctt    900
acaatagccc catctccagg ttgaggctag atggagggga cagagggaag tgacttgccc    960
aaggtgaccc aaactcccga gtgccagggc aggatctgaa ttcaggctct cagactgcag   1020
agcctgagtc cctccctgcc atgcctgtgc cagggtggaa atgtctggtc ctggagggga   1080
gcgtggactc ctggccttgg ctctggagac atcccctag accacgtggg ctcctaacct    1140
gtccatggtc actgtgctga ggggcgggac ggtgggtcac ccctagttct tttttcccca   1200
gggccagatt catggactga agggttgctc ggctctcaga gacccctaa gcgcccgcc    1260 ctggccccaa gccctccccc agctcccgcg tccccccct cctggcgctg actccgggcc   1320
agaagaggaa aggctgtctc cacccacctc tcgcactctc ccttctcctt tataaaggcc   1380
ggaacagctg aaagggtggc aacttctcct cctgcagccg ggagcggcct gcctgcctcc   1440
ctgcgcaccc gcagcctccc ccgctgcctc cctagagtcg acctgcagcc caagctt     1497
```

THERAPEUTIC AGENT FOR NEURODEGENERATIVE DISEASE

CROSS-REFERENCE TO RELATED APPLICATIONS

This patent application is the U.S. national phase of International Patent Application No. PCT/JP2019/038530, filed Sep. 30, 2019, which claims the benefit of Japanese Patent Application No. 2018-186759, filed on Oct. 1, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,922 bytes ASCII (Text) file named "753153SequenceListing.txt," created Mar. 24, 2021.

TECHNICAL FIELD

The present invention relates to a therapeutic agent for neurodegenerative diseases and the like. More particularly, it relates to a therapeutic agent for neurodegenerative diseases, containing an apoptosis inhibitor of macrophage (AIM) as an active ingredient and a method using same for the treatment or prophylaxis of neurodegenerative diseases.

BACKGROUND ART

Neurodegenerative diseases such as Alzheimer's disease, motor neuron disease and the like are diseases that exhibit progressive and refractory cognitive dysfunction and motor dysfunction due to degeneration and loss of specific nerves. While various neurodegenerative diseases are known, a common pathological feature of such neurodegenerative diseases is the accumulation of abnormal proteins, and the accumulation is considered to be the main pathology of neurodegeneration. Therefore, as a therapeutic or preventive approach for neurodegenerative diseases, the construction of means for removing or suppressing the accumulation of such abnormal proteins has been studied.

Alzheimer's disease is one of the representative diseases included in neurodegenerative diseases. It is known that plaque formation of amyloid β occurs first in the brain of patients with Alzheimer's disease, and then acetylation and coagulation of tau protein, loss of prolyl isomerase Pin1 and the like occur. Thus, it is considered that Alzheimer's disease can be treated and/or prevented by means for removing the accumulation of amyloid β in the early stage of the disease and/or means for suppressing the accumulation of the protein. In fact, many candidate substances for a therapeutic agent for Alzheimer's disease have been reported (patent documents 1-3).

AIM (also referred to as CD5L) is a factor which is specifically produced by a macrophage identified by the present inventors and suppresses apoptosis of the macrophage itself (non-patent document 1), and its association with several diseases has been suggested so far. For example, the blood concentration of AIM increases with obesity, and AIM is taken up by adipocytes due to CD36-mediated endocytosis and induces lipolysis of accumulated neutral fats, which suggests relationship with antiobesity (non-patent document 2). AIM releases free fatty acid from adipocytes by lipolysis of neutral fats, and the released fatty acid induces/maintains chronic inflammation in adipose tissue via stimulation of toll-like receptors. Metabolic syndrome is based on the acquisition of insulin resistance associated with obesity. Since chronic inflammation in adipose tissue is important, AIM is said to be associated with metabolic syndrome (non-patent document 3). The present inventors also clarified that AIM suppresses the differentiation of fat progenitor cells into mature adipocytes and induces the decomposition of fat droplets in adipocytes, and reported the possibility of application of AIM to obesity (patent document 4). Furthermore, the present inventors clarified that obese AIM knockout (KO) mice loaded with a high-calorie diet show pathology similar to human NASH pathology, such as obesity, fatty liver, fibrosis of liver parenchyma, and carcinogenesis, and reported the possibility of application of AIM to liver diseases (patent document 5). In addition, the present inventors clarified that AIM KO mice that underwent bilateral transient renal ischemia reperfusion developed acute renal failure, followed by the accumulation of necrotic renal tubular cells and the accompanying rapid progression of renopathy, and exacerbation of the systemic condition, and a high frequency of death was confirmed. The inventors showed that when AIM was administered to the AIM KO mice, BUN level was improved, renal function was rapidly improved, and systemic symptoms and mortality were also improved, and reported the possibility of the treatment of acute renal failure and the prophylaxis or treatment of chronic renal diseases by the supplementation of AIM (patent document 6). However, there have been no reports on the relationship between AIM and neurodegenerative diseases.

DOCUMENT LIST

Patent Documents patent document 1: JP5765857B
patent document 2: JP5692073B
patent document 3: WO 00/24392
patent document 4: WO 2010/140531
patent document 5: WO 2013/162021
patent document 6: WO 2015/119253

Non-Patent Documents non-patent document 1: Miyazaki, J Exp Med 189:413-422, 1999
non-patent document 2: Kurokawa, Cell Metab 11:479-492, 2010
non-patent document 3: Kurokawa, PNAS 108:12072-12077, 2011

SUMMARY OF INVENTION

Technical Problem

The present invention aims to provide a novel treatment method or prophylactic method using AIM protein for neurodegenerative diseases.

Solution to Problem

The present inventors have conducted intensive studies of the above-mentioned problem and found that (1) microglia, which are macrophages in the brain, do not produce AIM, (2) AIM cannot cross the Blood-Brain Barrier (BBB), (3)

when recombinant AIM protein is administered by microinjection into the brain of Alzheimer's disease model mice (5×FAD mice), the AIM protein accumulates in amyloid plaque,
(4) amyloid plaques are remarkably decreased by expressing AIM in the hippocampal region of 5×FAD mice by using adeno-associated virus, and (5) phagocytosis of multimeric amyloid β by brain-derived microglia is remarkably promoted by binding recombinant AIM protein to multimeric amyloid β in vitro and the like. Based on such findings, they have conducted further studies and the completed the present invention. That is, the present invention provides the following.

[1] An agent for the treatment or prophylaxis of a neurodegenerative disease, comprising an apoptosis inhibitor of macrophage (AIM), an AIM fragment having a biological activity of AIM, or a nucleic acid encoding the AIM or AIM fragment.

[2] The agent of [1], wherein the nucleic acid encoding AIM or AIM fragment is incorporated in a viral vector.

[3] The agent of [2], wherein the viral vector is a viral vector selected from the group consisting of adeno-associated virus, adenovirus, lentivirus, and Sendai virus.

[4] The agent of [3], wherein the viral vector is an adeno-associated virus.

[5] The agent of [4], wherein the adeno-associated virus is AAV serotype 5 (AAV5) or AAV serotype 9 (AAV9).

[6] The agent of any of [1] to [5], wherein the neurodegenerative disease is selected from the group consisting of Alzheimer's disease, Parkinson's disease, Lewy body dementia, frontotemporal dementia, multiple system atrophy, Pick disease, corticobasal degeneration, progressive supranuclear paralysis, amyotrophic lateral sclerosis, spinobulbar muscular atrophy, spinal progressive muscular atrophy, Huntington's disease, spinocerebella degeneration, hippocampus sclerosis, progressive myoclonus epilepsy, and dentatorubral-pallidoluysian atrophy.

[7] A method for treating or preventing a neurodegenerative disease, comprising administering AIM, an AIM fragment having a biological activity of AIM, or a nucleic acid encoding the AIM or AIM fragment to a subject.

[8] The method of [7], wherein the nucleic acid encoding AIM or AIM fragment is incorporated in a viral vector.

[9] The method of [8], wherein the viral vector is a viral vector selected from the group consisting of adeno-associated virus, adenovirus, lentivirus, and Sendai virus.

[10] The method of [8], wherein the viral vector is an adeno-associated virus.

[11] The method of [10], wherein the adeno-associated virus is AAV serotype 5 (AAV5) or AAV serotype 9 (AAV9).

[12] The method of any of [7] to [11], wherein the neurodegenerative disease is selected from the group consisting of Alzheimer's disease, Parkinson's disease, Lewy body dementia, frontotemporal dementia, multiple system atrophy, Pick disease, corticobasal degeneration, progressive supranuclear paralysis, amyotrophic lateral sclerosis, spinobulbar muscular atrophy, spinal progressive muscular atrophy, Huntington's disease, spinocerebella degeneration, hippocampus sclerosis, progressive myoclonus epilepsy, and dentatorubral-pallidoluysian atrophy.

[13] An apoptosis inhibitor of macrophage (AIM), an AIM fragment having a biological activity of AIM, or a nucleic acid encoding the AIM or AIM fragment for use in a method for treating or preventing a neurodegenerative disease.

[14] The apoptosis inhibitor, the AIM fragment, or the nucleic acid of [13], wherein the nucleic acid encoding AIM or AIM fragment is incorporated in a viral vector.

[15] The apoptosis inhibitor, the AIM fragment, or the nucleic acid of [2], wherein the viral vector is a viral vector selected from the group consisting of adeno-associated virus, adenovirus, lentivirus, and Sendai virus.

[16] The apoptosis inhibitor, the AIM fragment, or the nucleic acid of [15], wherein the viral vector is an adeno-associated virus.

[17] The apoptosis inhibitor, the AIM fragment, or the nucleic acid of [16], wherein the adeno-associated virus is AAV serotype 5 (AAV5) or AAV serotype 9 (AAV9).

[18] The apoptosis inhibitor, the AIM fragment, or the nucleic acid of any of [13] to [17], wherein the neurodegenerative disease is selected from the group consisting of Alzheimer's disease, Parkinson's disease, Lewy body dementia, frontotemporal dementia, multiple system atrophy, Pick disease, corticobasal degeneration, progressive supranuclear paralysis, amyotrophic lateral sclerosis, spinobulbar muscular atrophy, spinal progressive muscular atrophy, Huntington's disease, spinocerebella degeneration, hippocampus sclerosis, progressive myoclonus epilepsy, and dentatorubral-pallidoluysian atrophy.

[19] Use of an apoptosis inhibitor of macrophage (AIM), an AIM fragment having a biological activity of AIM, or a nucleic acid encoding the AIM or AIM fragment in the production of a medicament for the treatment or prophylaxis of a neurodegenerative disease.

[20] The use of [19], wherein the nucleic acid encoding AIM or AIM fragment is incorporated in a viral vector.

[21] The use of [20], wherein the viral vector is a viral vector selected from the group consisting of adeno-associated virus, adenovirus, lentivirus, and Sendai virus.

[22] The use of [21], wherein the viral vector is an adeno-associated virus.

[23] The use of [22], wherein the adeno-associated virus is AAV serotype 5 (AAV5) or AAV serotype 9 (AAV9).

[24] The use of any of [19] to [23], wherein the neurodegenerative disease is selected from the group consisting of Alzheimer's disease, Parkinson's disease, Lewy body dementia, frontotemporal dementia, multiple system atrophy, Pick disease, corticobasal degeneration, progressive supranuclear paralysis, amyotrophic lateral sclerosis, spinobulbar muscular atrophy, spinal progressive muscular atrophy, Huntington's disease, spinocerebella degeneration, hippocampus sclerosis, progressive myoclonus epilepsy, and dentatorubral-pallidoluysian atrophy.

Advantageous Effects of Invention

According to the present invention, accumulation of abnormal proteins in the brain of a subject can be suppressed. As a result, neurodegenerative diseases including Alzheimer's disease which are caused by the accumulation of abnormal proteins can be treated or prevented.

DESCRIPTION OF EMBODIMENTS

Figure 1:
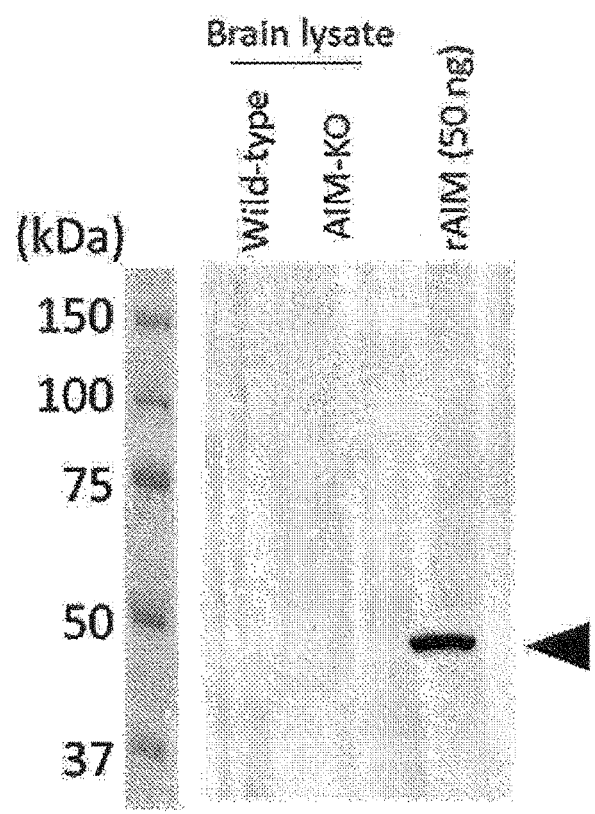
FIG. 1 AIM expression in the brain was confirmed by Western blotting using a lysate of the whole mouse brain. Brain lysates (20 ng/lane) of wild-type C57BL/6 mouse (Lane 1: Wild-type), AIM-deficient mouse (Lane 2: AIM-KO) and recombinant AIM protein (50 ng) as a positive control were fractionated by SDS-PAGE, and Western blotting was performed using an anti-AIM antibody. No expression of AIM was observed in the brain of wild-type mice or AIM-deficient mice.

The present invention is explained in detail in the following.

1. Agent for Treatment or Prophylaxis of Neurodegenerative Disease

The present invention provides an agent for the treatment or prophylaxis of a neurodegenerative disease, containing AIM, an AIM fragment having a biological activity of AIM, or a nucleic acid encoding the AIM or AIM fragment (hereinafter sometimes to be referred to as "the agent of the present invention").

AIM to be used in the present invention is a protein containing an amino acid sequence that is the same or substantially the same as the amino acid sequence shown in SEQ ID NO: 1 (amino acid sequence of human-derived AIM protein). AIM may be, for example, a protein isolated and purified from macrophage, which is immunocyte of warm-blooded animals (e.g., human, mouse, rat, rabbit, sheep, swine, bovine, horse, cat, dog, monkey, chimpanzee, chicken and the like). It may also be a protein chemically synthesized or biochemically synthesized in a cell-free translation system. Alternatively, the protein may be a recombinant protein produced from a transformant incorporating a nucleic acid comprising a base sequence that encodes the above-described amino acid sequence. The species of organism to be the origin of the AIM to be used in the present invention may be preferably the same as the species of the subject suffering from a neurodegenerative disease. For example, when the application target of the agent of the present invention is a human, human AIM is preferably used.

Substantially the same amino acid sequence as the amino acid sequence shown in SEQ ID NO:1 refers to an amino acid sequence having an identity or similarity of about 60% or more, preferably about 70% or more, further preferably about 80% or more, particularly preferably about 90% or more, most preferably about 95% or more, to the amino acid sequence shown in SEQ ID NO:1, and the like. As used herein, the "identity" means the proportion (%) of the same amino acids and similar amino acid residues to the overlapping total amino acid residues in the optimal alignment (preferably, the algorithm can consider, for the optimal alignment, introduction of a gap into one or both of the sequences), when two amino acid sequences are aligned using mathematical algorithm known in the technical field. The "similarity" means the ratio (%) of the number of positions where the same or similar amino acid residues are present in two amino acid sequences when they are aligned to the total number of amino acid residues. The "similar amino acid" means amino acids similar in physicochemical properties and, for example, amino acids classified into the same group such as aromatic amino acid (Phe, Trp, Tyr), aliphatic amino acid (Ala, Leu, Ile, Val), polar amino acid (Gln, Asn), basic amino acid (Lys, Arg, His), acidic amino acid (Glu, Asp), amino acid having hydroxyl group (Ser, Thr), amino acid with small side chain (Gly, Ala, Ser, Thr, Met) and the like can be mentioned. Substitution with such similar amino acids is predicted to cause no change in the phenotype of the protein (i.e., conservative amino acid substitution). Specific examples of the conservative amino acid substitution are well known in the art and described in various documents (see, for example, Bowie et al., Science, 247:1306-1310(1990)).

The identity or similarity of the amino acid sequence in the present specification can be calculated using the identity or similarity calculation algorithm NCBI BLAST (National Center for Biotechnology Information Basic Local Alignment Search Tool) under the following conditions (expectancy=10; gap; matrix=BLOSUM62; filtering=OFF). Examples of other algorithm to determine the identity or similarity of amino acid sequence include the algorithm described in Karlin et al., Proc. Natl. Acad. Sci. USA, 90:5873-5877(1993) [the algorithm is incorporated in NBLAST and XBLAST program (version 2.0) (Altschul et al., Nucleic Acids Res., 25:3389-3402(1997))], the algorithm described in Needleman et al., J. Mol. Biol., 48:444-453(1970) [the algorithm is incorporated in GAP program in GCG software package], the algorithm described in Myers and Miller, CABIOS, 4:11-17(1988) [the algorithm is incorporated in ALIGN program (version 2.0) which is a part of the CGC sequence alignment software package], the algorithm described in Pearson et al., Proc. Natl. Acad. Sci. USA, 85: 2444-2448(1988) [the algorithm is incorporated in FASTA program in the GCG software package] and the like, and they can also be preferably used in the same manner. More preferably, substantially the same amino acid sequence as the amino acid sequence shown in SEQ ID NO:1 is an amino acid sequence having an identity of about 60% or more, preferably about 70% or more, further preferably about 80% or more, particularly preferably about 90% or more, and most preferably about 95% or more, to the amino acid sequence shown in SEQ ID NO:1.

As a protein comprising substantially the same amino acid sequence as the amino acid sequence shown in SEQ ID NO:1, for example, a protein comprising substantially the same amino acid sequence as the aforementioned amino acid sequence shown in SEQ ID NO:1, and having substantially the same quality of activity as the biological activity of wild-type AIM can be mentioned. Examples of the biological activity of the wild-type AIM include endocytosis activity on macrophage (including microglia), activity to suppress apoptosis of macrophage, activity to maintain or promote arteriosclerosis, adipocyte differentiation suppressive activity, activity to melt lipid droplet of adipocyte, adipocyte reducing activity, CD36 binding activity, endocytosis activity to adipocyte, FAS binding activity, FAS function suppressive activity, antiobesity activity, activity to prevent or treat hepatic diseases (fatty liver, NASH, cirrhosis, liver cancer), activity to prevent or treat renal diseases (acute renal failure, chronic nephritis, chronic renal failure, nephrotic syndrome, diabetic nephropathy, nephrosclerosis, IgA nephropathy, hypertensive nephropathy, nephropathy with collagen disease or IgM nephropathy) and the like. In the present invention, particularly, an endocytosis activity on macrophage can be a preferable index. The activity can be confirmed using in vitro macrophage (or microglia) phagocytosis tests, though not limited thereto. In the present specification, the "substantially the same quality" means that the activity thereof is qualitatively (e.g., physiologically or pharmacologically) the same. Therefore, it is preferable that the aforementioned activities be equivalent to each other, but the quantitative factors of these activities, such as the extent of activity (e.g., about 0.1 to about 10 times, preferably about 0.5 to about 2 times) and the molecular weight of the protein, may be different. The aforementioned activities can be measured by a method known per se.

Examples of the AIM to be used in the present invention also include proteins comprising (1) an amino acid sequence having 1 or 2 or more (preferably about 1 to 100, preferably about 1 to 50, further preferably about 1 to 10, particularly preferably 1 to several (2, 3, 4 or 5)) amino acids deleted from the amino acid sequence shown in SEQ ID NO:1, (2) an amino acid sequence having 1 or 2 or more (preferably about 1 to 100, preferably about 1 to 50, further preferably about 1 to 10, particularly preferably 1 to several (2, 3, 4 or 5)) amino acids added to the amino acid sequence shown in SEQ ID NO:1, (3) an amino acid sequence having 1 or 2 or more (preferably about 1 to 50, preferably about 1 to 10, further preferably 1 to several (2, 3, 4 or 5)) amino acids inserted in the amino acid sequence shown in SEQ ID NO:1, (4) an amino acid sequence having 1 or 2 or more (preferably about 1 to 50, preferably about 1 to 10, further preferably 1 to several (2, 3, 4 or 5)) amino acids substituted by other amino acids in the amino acid sequence shown in SEQ ID NO:1, or (5) an amino acid sequence comprising a combination thereof. When an amino acid sequence has been inserted, deleted or substituted as described above, the position of the insertion, deletion or substitution is not particularly limited as long as a desired biological activity (e.g., endocytosis activity on macrophage (including microglia)) of the protein is maintained.

AIM in the present invention is preferably a human AIM protein having the amino acid sequence shown in SEQ ID NO:1 (GenBank Accession No.: AAD01446), or a homologue thereof in other mammals [for example, mouse homologue registered in the GenBank as Accession No.: AAD01445 and the like], more preferably, a human AIM protein consisting of the amino acid sequence shown in SEQ ID NO:1.

In the present specification, the protein and peptide are described according to conventional peptide lettering, and the left end is N-terminus (amino terminus), and the right end is C-terminus (carboxyl terminus). In AIM to be used in the present invention including a protein comprising the amino acid sequence shown in SEQ ID NO:1, the C-terminus may be any of a carboxyl group (—COOH), carboxylate (—COO$^-$), amide (—CONH$_2$) and ester (—COOR).

Here, as R in the ester, a $C_{1-6}$ alkyl group, for example, methyl, ethyl, n-propyl, isopropyl and n-butyl, a $C_{3-8}$ cycloalkyl group, for example, cyclopentyl and cyclohexyl, a $C_{6-12}$ aryl group, for example, phenyl and α-naphthyl, a phenyl-$C_{1-2}$ alkyl group, for example, benzyl and phenethyl, a $C_{7-14}$ aralkyl group, for example, an α-naphthyl-$C_{1-2}$ alkyl group, for example, α-naphthylmethyl, a pivaloyloxymethyl group; and the like can be used.

When the AIM to be used in the present invention has a carboxyl group (or carboxylate) at a position other than the C-terminus, a protein wherein the carboxyl group is amidated or esterified is also included in the protein of the present invention. In this case, as the ester, the above-described ester at the C terminus, and the like, for example, is used.

Furthermore, the AIM in the present invention also includes a protein wherein the amino group of the N-terminal amino acid residue is protected by a protecting group (e.g., $C_{1-6}$ acyl groups such as $C_{1-6}$ alkanoyls such as formyl group and acetyl group, and the like); a protein wherein the glutamine residue that may be produced upon cleavage at the N terminus in vivo has been converted to pyroglutamic acid, a protein wherein a substituent (e.g., —OH, —SH, amino group, imidazole group, indol group, guanidino group and the like) on a side chain of an amino acid in the molecule is protected by an appropriate protecting group (e.g., $C_{1-6}$ acyl groups such as $C_{1-6}$ alkanoyl groups such as formyl group and acetyl group, and the like), a conjugated peptide such as what is called a glycopeptide having a sugar chain bound thereto, and the like.

In the present specification, the "AIM" is a concept including not only wild-type AIM but also mutants of these and the like having an activity substantially the same or improved than the biological activity of the wild-type AIM. Here, the "activity of substantially the same quality" is as defined above. In addition, the "activity of substantially the same quality" can be measured in the same manner as in the case of AIM.

One embodiment of the mutant of AIM includes, but is not limited to, the following.

The mutant human AIM of the present invention preferably contains the amino acid sequence of any one of the following (1b) to (5b).

(1b) an amino acid sequence wherein cysteine at amino acid number 191 of the amino acid sequence shown in SEQ ID NO: 1 is substituted with serine,
(2b) an amino acid sequence wherein cysteine at amino acid number 300 of the amino acid sequence shown in SEQ ID NO: 1 is substituted with serine,
(3b) an amino acid sequence wherein cysteine at amino acid number 191 of the amino acid sequence shown in SEQ ID NO: 1 is substituted with serine, and an amino acid sequence wherein cysteine at amino acid number 300 of the amino acid sequence shown in SEQ ID NO: 1 is substituted with serine,
(4b) an amino acid sequence substantially the same as the amino acid sequence of any one of (1b) to (3b), wherein cysteines present in the amino acid sequence of any one of (1b) to (3b) and the substituted serine remain,
(5b) an amino acid sequence further comprising deletion, addition, insertion or substitution of one to several amino acids or a combination thereof at a position(s) other than cysteines present in the amino acid sequence of any one of (1b) to (3b) and the substituted serine.

As an AIM mutant having a function the same as or improved than the function of the wild-type recombinant AIM, one disclosed in Patent Application No. JP2017-220733 or the like can be used.

As a component of the agent of the present invention, not only AIM but also an AIM fragment having the biological activity of AIM can also be used. Whether or not the AIM fragment has the biological activity of wild-type AIM may be determined by the aforementioned method.

As one embodiment of an AIM fragment, since intact AIM protein contains 3 SRCR (Scavenger-Receptor Cysteine-Rich) domains containing a large amount of cysteine, each SRCR domain can be recited as an example of an AIM fragment having substantially the same quality of activity as the biological activity possessed by the wild-type AIM. To be specific, for example, of the amino acid sequence shown in SEQ ID NO:1, partial amino acid sequences respectively comprising SRCR1 domain (amino acid Nos. 24-125 of the amino acid sequence shown in SEQ ID NO:1), SRCR2 domain (amino acid Nos. 138-239 of the amino acid sequence shown in SEQ ID NO:1), and SRCR3 domain (amino acid Nos. 244-346 of the amino acid sequence shown in SEQ ID NO:1), partial amino acid sequence comprising any combination of SRCR domains and the like can be used as the AIM fragment. The size of the AIM fragment having substantially the same quality of activity as the biological activity possessed by the wild-type AIM is not particularly limited as long as it comprises the above-mentioned functional domain. The partial peptide preferably comprises not less than 50 partial amino acid sequences, more preferably not less than 100 partial amino acid sequences, further preferably not less than 200 partial amino acid sequences. The partial amino acid sequences may be a single consecutive partial amino acid sequence, or discontinuous plural partial amino acid sequences linked to each other.

In addition, the C-terminus of the AIM fragment to be used in the present invention may be any of a carboxyl group (—COOH), carboxylate (—COO⁻), amide (—CONH₂) and ester (—COOR). Here, examples of the R in ester include, those similar to the examples recited above for AIM. When the partial peptide of the present invention has a carboxyl group (or carboxylate) at a position other than the C-terminus, the carboxyl group may be amidated or esterified, which is also encompassed in the partial peptide of the present invention. As the ester in this case, for example, those similar to the ester at the C-terminus and the like are used.

Furthermore, the AIM fragment to be used in the present invention includes, in the same manner as in the above-mentioned AIM, the amino group of the N-terminal amino acid residue may be protected with a protecting group, the glutamine residue at the N-terminus may be converted to pyroglutamic acid, a substituent on the side chain of the amino acid in a molecule may be protected with a suitable protecting group, or the partial peptide may be a composite peptide wherein a sugar chain is bonded (so-called glycopeptide and the like), and the like.

The AIM (including AIM fragment) to be used in the present invention may be in the form of a salt. For example, salts with physiologically acceptable acid (e.g., inorganic acid, organic acid), base (e.g., alkali metal salt) and the like are used, and a physiologically acceptable acid addition salt is particularly preferable. Examples of such salt to be used include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

AIM can be produced from a macrophage of the aforementioned mammals by a protein purification method known per se. To be specific, AIM or a salt thereof can be prepared by homogenizing mammalian macrophage, removing cell debris by low-speed centrifugation, centrifuging the supernatant at a high speed to precipitate a cellular membrane-comprising fraction, and subjecting the supernatant to chromatography such as reversed-phase chromatography, ion exchange chromatography, affinity chromatography and the like, and the like.

AIM (including AIM fragments) can also be produced according to a publicly known method of peptide synthesis. The method of peptide synthesis may be any of, for example, a solid phase synthesis process and a liquid phase synthesis process. A desired protein can be produced by condensing a partial peptide or amino acid capable of constituting AIM with the remaining portion, and removing any protecting group the resultant product may have.

Here, the condensation and the protecting group removal are conducted in accordance with methods known per se, for example, the methods indicated in (1) and (2) below:
(1) M. Bodanszky and M. A. Ondetti: *Peptide Synthesis*, Interscience Publishers, New York (1966)
(2) Schroeder and Luebke: *The Peptide*, Academic Press, New York (1965).

AIM thus obtained can be purified or isolated by a known method of purification. Here, as examples of the method of purification, solvent extraction, distillation, column chromatography, liquid chromatography, recrystallization, combinations thereof and the like can be mentioned.

When thus obtained AIM is in a free form, the free form can be converted into a suitable salt form by a known method or a method based thereon, and on the other hand, when the AIM is obtained in the form of a salt, it can be converted into the free form or in the form of a different salt by a known method or a method based thereon.

Furthermore, AIM can also be produced by culturing a transformant comprising a nucleic acid encoding the same, and separating and purifying AIM from the obtained culture. The nucleic acid encoding AIM or AIM fragment may be DNA or RNA, or DNA/RNA chimera, preferably DNA. Additionally, the nucleic acid may be double-stranded or single-stranded. In the case of a double-stranded nucleic acid, it may be a double-stranded DNA, a double-stranded RNA, or a DNA:RNA hybrid. In the case of a single strand, it may be a sense strand (that is, coding strand), or an antisense strand (that is, non-coding strand).

Examples of the DNA encoding AIM (including AIM fragments) include genomic DNA, cDNA derived from macrophage of warm-blooded animal (e.g., human, bovine, monkey, horse, swine, sheep, goat, dog, cat, guinea pig, rat, mouse, rabbit, hamster, chicken and the like), synthetic DNA and the like. Genomic DNA encoding AIM or an AIM fragment can be directly amplified by Polymerase Chain Reaction (hereinafter to be abbreviated as "PCR method") by using, as a template, a genomic DNA fraction prepared from any cell of the aforementioned animals [for example, hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immunocyte (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding progenitor cell, stem cell or cancer cell thereof, and the like], or any tissue where such cells are present [for example, brain or any portion of the brain (e.g., olfactory bulb, amygdaloid nucleus, basal ganglia, hippocampus, thalamus, hypothalamus, subthalamic nucleus, cerebral cortex, medulla oblongata, cerebellum), spinal cord, hypophysis, stomach, pancreas, kidney, liver, gonad, thyroid, gall-bladder, bone marrow, adrenal gland, skin, lung, gastrointestinal tract (e.g., large intestine, small intestine), blood vessel, heart, thymus, spleen, submandibular gland, peripheral blood, prostate, testicle, ovary, placenta, uterus, bone, joint, adipose tissue (e.g., brown adipose tissue, white adipose tissue), skeletal muscle and the like], and cDNA encoding AIM or an AIM fragment can also be directly amplified by PCR method and Reverse Transcriptase-PCR (hereinafter to be abbreviated as "RT-PCR method") by using, as a template, a total RNA or mRNA fraction prepared from macrophage, respectively. Alternatively, the genomic DNA and cDNA encoding AIM or a peptide fragment thereof can also be cloned by colony or plaque hybridization method or PCR method and the like from a genomic DNA library and cDNA library prepared by inserting the above-mentioned genomic DNA and total RNA or a fragment of mRNA into a suitable vector. The vector used for the library may be any of a bacteriophage, a plasmid, a cosmid, a phagemid and the like.

Examples of the nucleic acid encoding AIM include a nucleic acid comprising the same or substantially the same base sequence as the base sequence shown in SEQ ID NO: 2 and the like. As the nucleic acid comprising the same or substantially the same base sequence as the base sequence shown in SEQ ID NO: 2, for example, a nucleic acid comprising a base sequence having an identity or similarity of not less than about 60%, preferably not less than about 70%, more preferably not less than about 80%, particularly preferably not less than about 90%, with the base sequence shown in SEQ ID NO: 2, and encoding a protein having an activity of substantially the same quality as the aforementioned AIM and the like can be used. In one embodiment, the nucleic acid comprising the same or substantially the same base sequence as the base sequence shown in SEQ ID NO: 2 is a nucleic acid comprising a base sequence having a homology of not less than about 60%, preferably not less than about 70%, more preferably not less than about 80%, particularly preferably not less than about 90%, with the base sequence shown in SEQ ID NO: 2, and encoding a protein having the same or substantially the same quality of activity as the aforementioned AIM. The nucleic acid encoding AIM also includes a nucleic acid sequence subjected to codon optimization for the purpose of increasing expression efficiency in an organism to be the application target.

The identity or similarity of the base sequence in the present specification can be calculated under the following conditions (an expectation value=10; gaps are allowed; filtering=ON, match score=1; mismatch score=−3) using an identity or similarity scoring algorithm NCBI BLAST (National Center for Biotechnology Information Basic Local Alignment Search Tool). As other algorithm for determining the identity or similarity of the base sequence, for example, the above-mentioned homology calculation algorithm for amino acid sequences can be similarly preferably recited as the example.

The nucleic acid encoding AIM is preferably a nucleic acid comprising a base sequence encoding human AIM protein shown by the base sequence shown in SEQ ID NO: 2 (GenBank accession No: AF011429), or a homologue thereof in other mammal [for example, mouse homologue registered in GenBank as accession No: AF011428 and the like].

As the component of the agent of the present invention, a nucleic acid encoding AIM, or an AIM fragment having a biological activity of AIM can also be used.

The nucleic acid encoding AIM or AIM fragment to be used in the present invention may be any as long as it comprises a base sequence encoding a peptide comprising the same or substantially the same amino acid sequence as a part of the amino acid sequence shown in SEQ ID NO:1. Specifically, as a nucleic acid encoding the AIM fragment, (1) a nucleic acid comprising a partial base sequence of the base sequence shown in SEQ ID NO: 2, or (2) a nucleic acid comprising a base sequence having an identity or similarity of not less than about 60%, preferably not less than about 70%, more preferably not less than about 80%, particularly preferably not less than about 90%, with a nucleic acid comprising a partial base sequence of the base sequence shown in SEQ ID NO: 2, and encoding a protein having an activity of substantially the same quality as the aforementioned AIM and the like are used.

The nucleic acid encoding AIM or AIM fragment can be cloned by amplifying same using a synthesized DNA primer having a part of a base sequence encoding the AIM or AIM fragment by PCR method, or by conducting hybridization of a DNA incorporated into a suitable expression vector with a labeled DNA fragment or synthetic DNA encoding a part or whole region of AIM. Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

As examples of the highly stringent conditions, conditions of a hybridization reaction in 6×SSC (sodium chloride/sodium citrate) at 45° C. followed by washing in 0.2×SSC/0.1% SDS at 65° C. once or more and the like can be mentioned. Those skilled in the art are able to easily obtain desired stringency by changing the salt concentration of the hybridization solution, hybridization reaction temperature, probe concentration, probe length, the number of mismatches, hybridization reaction time, the salt concentration of the washing solution, washing temperature and the like as appropriate. When a commercially available library is used, hybridization can be conducted according to the method described in the instruction manual attached to the library.

The nucleic acid encoding AIM or AIM fragment may also be functionally linked to an expression vector or the like having a promoter that is specifically expressed in the brain. By delivering an expression vector containing a nucleic acid encoding AIM or AIM fragment into the brain, the AIM or AIM fragment can be specifically expressed in the brain. Examples of the brain specific promoter include, but are not limited to, SCG10, GFAP promoter, synapsin 1 promoter, tubulin α1 promoter, calcium/calmodulin-dependent protein kinase II promoter, neuron-specific enolase promoter, PDGF (platelet-derived growth factor beta)-β chain promoter and the like.

In one preferable embodiment, a nucleic acid encoding AIM or AIM fragment may be mounted on a viral vector. Preferable examples of the viral vector include, but are not limited to, adeno-associated virus, adenovirus, lentivirus, and Sendai virus. In consideration of the use in gene therapy, adeno-associated virus is preferable because it can express transgene for a long period of time, is highly safe because it is derived from a non-pathogenic virus and the like. In addition, the serotype of the adeno-associated virus is not particularly limited as long as the desired effect of the present invention can be obtained, and any of serotypes 1, 2, 3, 4, 5, 6, 7, 8, 9, and 10 may also be used. Particularly, considering the high expression efficiency in neural tissues, serotype 1, 2, 5, 9, or 10 is preferable (see WO 2005/033321 for various serotypes of AAV). Furthermore, AAV5 is more preferable from the aspect of high expression efficiency, and serotype 9 (AAV9) is more preferable from the aspect of the property of efficient permeation through the blood vessel brain barrier (Iwata N et al, Sci Rep. 2013; 3:1472). The viral vector to be used in the present invention also includes variants thereof. As a variant of a viral vector, a modified capsid and the like are known. Particularly, examples of the AAV variant include, but are not limited to, those disclosed in WO 2012/057363 and the like.

When a nucleic acid encoding AIM or AIM fragment is mounted into a viral vector, for the purpose of specifically expressing AIM or AIM fragment in the target brain, it is preferable to use a brain-specific promoter as a promoter that controls the expression of the nucleic acid encoding AIM or AIM fragment. Examples of such brain-specific promoter include, but are not limited to, SCG10, GFAP promoter, synapsin 1 promoter, tubulin α1 promoter, calcium/calmodulin-dependent protein kinase II promoter, neuron-specific enolase promoter, PDGF (platelet-derived growth factor beta)-β chain promoter and the like. In addition to the promoter, known sequences such as Poly A addition signal, Kozak consensus sequence, tag sequence, linker sequence, NLS and the like may also be mounted as appropriate into a viral vector together with the nucleic acid encoding AIM or AIM fragment according to the purpose.

A viral vector containing a nucleic acid encoding AIM or AIM fragment can be prepared by a known method. In brief, a plasmid vector for virus expression is prepared by inserting a nucleic acid encoding AIM or AIM fragment and, if necessary, a nucleic acid having a desired function (e.g., brain-specific promoter, etc.), this is transfected into an appropriate host cell to transiently produce a viral vector containing the polynucleotide of the present invention, and the viral vector is recovered.

For example, when AAV vector is prepared, a vector plasmid is created first in which the ITRs at both ends of a wild-type AAV genome sequence are left and, in the place of a DNA encoding the other Rep proteins and capsid proteins, a nucleic acid encoding AIM or AIM fragment is inserted. On the other hand, the DNAs encoding Rep proteins and capsid proteins, which is necessary for forming virus particles, are inserted into another plasmid. Furthermore, a plasmid containing genes (E1A, E1B, E2A, VA, and E4orf6) responsible for the adenovirus helper action necessary for the proliferation of AAV is prepared as an adenovirus helper plasmid. These three plasmids are co-transfected into a host cell, whereby recombinant AAV (i.e., AAV vector) is produced within the cell. As the host cell, it is preferable to use a cell (e.g., 293 cell, etc.) that can supply a part of the gene product(s) (proteins) of the gene(s) responsible for the aforementioned helper action, and when such a cell is used, it is not necessary to mount the gene encoding the protein(s) that can be supplied from the host cell on the aforementioned adenovirus helper plasmid. Since the produced AAV vector exists in the nucleus, the host cell is frozen and thawed and recovered, and separated and purified by density ultracentrifugation method using cesium chloride, column method, and the like, whereby the desired AAV vector is prepared.

When the agent of the present invention is used to treat or prevent a neurodegenerative disease of a subject, the route of administration thereof is not particularly limited as long as the delivery of the active ingredient AIM protein into the brain is realized. In one embodiment, when the component contained in the agent of the present invention is AIM protein, considering that the AIM protein does not cross the Blood-Brain Barrier (BBB), a pinhole may be made in the cranial bone of the subject, and the agent of the present invention is directly injected into the brain tissue by a method known per se, such as microinjection or the like. Alternatively, the AIM protein can also be delivered into the brain by encapsulating the AIM protein in a liposome modified to permit permeation through the Blood-Brain Barrier and administering same to the subject by intravenous administration or the like. Also, even when the component contained in the agent of the present invention is a nucleic acid encoding AIM protein, the nucleic acid encoding the AIM protein can be delivered into the brain by a method of directly introducing the agent of the present invention from a pinhole provided in the cranial bone of a subject, a method using the aforementioned liposome, or the like.

When the component of the agent of the present invention is a viral vector mounting a nucleic acid encoding AIM, a pinhole is provided in the cranial bone of a subject, and the agent of the present invention can be directly introduced into the brain tissue via the pinhole by a method known per se, such as microinjection. As mentioned above, use of AAV9 is highly preferable since AIM can be specifically expressed in the brain of the subject simply by injecting the agent of the present invention into the circulating blood without providing a pinhole in the cranial bone of the subject. That is, in an embodiment using means capable of crossing the Blood-Brain Barrier such as liposome, AAV9 and the like, the agent of the present invention is parenterally administered and can be administered by, for example, intravenous administration, intraarterial administration, subcutaneous administration, or intraperitoneal administration.

When the agent of the present invention is formulated for parenteral administration, for example, it can be formulated as injection, suppository or the like. The injection may include the dosage forms of intravenous injection, subcutaneous injection, intradermal injection, intramuscular injection, drip injection, and the like. Such injection can be prepared according to a known method. Injection can be prepared, for example, by dissolving, suspending or emulsifying components such as AIM, nucleic acid encoding AIM and/or virus mounting a nucleic acid encoding AIM and the like in a sterile aqueous solution or an oily solution generally used for injection. As the aqueous solution for injection, for example, saline, isotonic solution containing glucose and other auxiliary agents, and the like are used, which may be used in combination with a suitable solubilizing agent, for example, alcohol (e.g. ethanol), polyalcohol (e.g., propylene glycol, polyethylene glycol), non-ionic surfactant [e.g., polysorbate80, HCO-50 (polyoxyethylene (50 mol) adduct of hydrogenated castor oil)] and the like. As the oily solution, sesame oil, soybean oil and the like are used and, as a solubilizing agent, benzyl benzoate, benzyl alcohol and the like may be used in combination. A prepared injection is preferably filled in a suitable ampoule.

The neurodegenerative disease to be treated or prevented by the agent of the present invention is not particularly limited as long as it is caused by the accumulation of abnormal protein in the brain. In the present specification, the "abnormal protein" includes proteins that can cause diseases as a result of loss, reduction, enhancement, or change in the original biological function due to changes in three-dimensional structure caused by gene mutation, chemical modification and the like, and also includes protein aggregates that abnormally coagulate or accumulate, even if the individual protein is the same as a normal protein, to form abnormal protein aggregates as a whole, resulting in protein aggregates that can cause diseases. The neurodegenerative diseases to be treated or prevented using the agent of the present invention include, but are not limited to, Alzheimer's disease, Parkinson's disease, Lewy body dementia, frontotemporal dementia, multiple system atrophy, Pick disease, corticobasal degeneration, progressive supranuclear paralysis, amyotrophic lateral sclerosis, spinobulbar muscular atrophy, spinal progressive muscular atrophy, Huntington's disease, spinocerebella degeneration, hippocampus sclerosis, progressive myoclonus epilepsy, and dentatorubral-pallidoluysian atrophy. In one embodiment, the disease to which the agent of the present invention is applied is Alzheimer's disease.

The dose of the agent of the present invention to a subject is not particularly limited as long as it is a therapeutically and/or prophylactically effective amount, and may be appropriately optimized according to the kind and form of the active ingredient, the age and body weight of the subject, the administration schedule, the administration method, and the like.

By applying the agent of the present invention to a subject suffering from a neurodegenerative disease, AIM or an AIM fragment is delivered into the brain of a subject or expressed in the brain of a subject. AIM or an AIM fragment in the brain binds to abnormal proteins present in the brain and marks the proteins as targets for removal. The marked abnormal proteins are rapidly removed from the brain by phagocytosis by microglia. As a result, the neurodegenerative disease in the subject can be treated and/or prevented.

The "treatment" of a disease in the present specification may include remission of the disease and improvement of the degree of the disease.

The "prophylaxis" of a disease in the present specification includes delaying the onset of the disease in addition to preventing the onset of the disease. In addition, the "prophylaxis" of a disease in the present specification also includes preventing the recurrence of the disease after treatment or delaying the recurrence of the disease after treatment.

2. Method for Treatment or Prophylaxis of Neurodegenerative Disease

The present invention also provides a method for treating or preventing a neurodegenerative disease, comprising administering AIM, an AIM fragment having a biological activity of AIM, or a nucleic acid encoding the AIM or AIM fragment to a subject (hereinafter sometimes referred to as "the method of the present invention").

In the method of the present invention, AIM and the like to be used as the active ingredient, administration means for each component and the like are the same as those explained in "1. Agent for treatment or prophylaxis of neurodegenerative disease".

The subject to which the method of the present invention is to be applied include any organism that can suffer from a neurodegenerative disease. Specific examples include warm-blooded animals such as human, bovine, monkey, horse, swine, sheep, goat, dog, cat, guinea pig, rat, mouse, rabbit, hamster, bird and the like. As described above, it is preferable to match the origin of the application subject with that of AIM and the like.

In one preferable embodiment of the present invention, a viral vector mounting a nucleic acid encoding AIM can also be provided. Usable viral vector and the like are the same as those explained in "1. Agent for treatment or prophylaxis of neurodegenerative disease".

The neurodegenerative diseases to be treated or prevented by the agent of the present invention are also the same as those explained in "1. Agent for treatment or prophylaxis of neurodegenerative disease".

The dose of each component such as AIM and the like in the method of the present invention is not particularly limited as long as it is a therapeutically and/or prophylactically effective amount, and may be appropriately optimized according to the kind and form of the active ingredient, the age and body weight of the subject, the administration schedule, the administration method, and the like.

The present invention is explained more specifically in the following Examples; however, the present invention is not limited in any way by these Examples.

EXAMPLE

[Example 1] Confirmation of Expression of AIM Protein in the Brain of Wild-Type Mouse The whole brains of wild-type C57BL/6 mouse (Lane 1: Wild-type) and AIM-deficient mouse (Lane 2: AIM-KO)

were homogenized in a Lysis Buffer to prepare lysates, 20 ng of protein was fractionated on SDS-PAGE together with positive control rAIM protein (50 ng), and then transferred to polyvinylidene fluoride (PDVF) membrane, and Western blotting was performed using an anti-AIM antibody (rabbit anti-mouse AIM anti-serum).

The results are shown in FIG. 1. As shown in FIG. 1, AIM expression was not observed in the brain of the wild-type mouse or AIM-deficient mouse.

[Example 2] Immunostaining of the Brain of Wild-Type Mouse

Brain tissue of wild-type C57BL/6 mouse was fixed with 4% para-form aldehyde and, after paraffin blocking, a 4 μm-thick section covering the main part of the brain was prepared. After a deparaffinizing treatment, immunostaining was performed using an anti-AIM antibody (rabbit anti-mouse AIM antiserum: an antibody that has been used for immunostaining), and detection was performed by the DAB chromogenic method using a peroxidase reaction.

Figure 2:
FIG. 2 AIM expression in the brain was confirmed immunohistochemically. Brain tissue sections (longitudinal slices) of wild-type C57BL/6 mice were immunostained with an anti-AIM antibody. Detection was performed by the DAB chromogenic method using a peroxidase reaction, but the expression of AIM was not observed.

The results are shown in FIG. 2. As shown in FIG. 2, AIM expression was not observed in the whole brain of the wild-type mouse.

[Example 3] Confirmation of AIM mRNA in the Brain of Wild-Type Mouse

RNA was extracted from each of the whole brain of wild-type C57BL/6 mouse (WT) (Lane 1), the whole brain of AIM-deficient mouse (AIM-KO) (Lane 2), the liver of WT mouse (positive control, Lane 3), the liver of AIM-KO mouse (Lane 4), microglia isolated and proliferated from the brain of WT newborn mouse (Lane 5), and microglia of the same AIM-KO (Lane 6), and the expression of AIM was analyzed by the quantitative RT-PCR method. Based on the expression in the liver as 1, the expression in each sample was shown in numerical value as relative expression.

Figure 3:
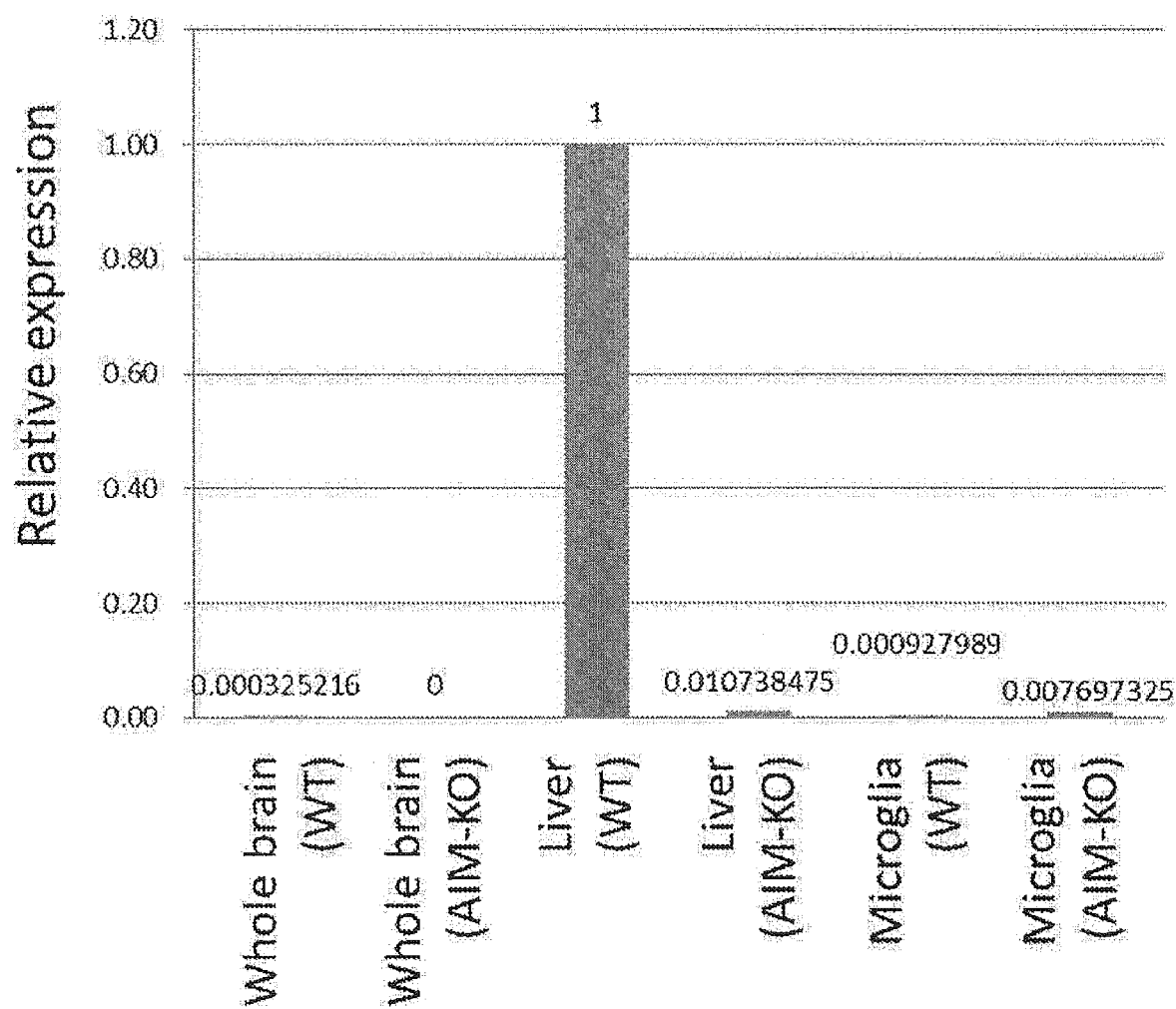
FIG. 3 The total RNA was extracted from each of the whole brain of wild-type C57BL/6 mouse (WT) (Lane 1), the whole brain of AIM-deficient mouse (AIM-KO) (Lane 2), the liver of WT mouse (positive control, Lane 3), the liver of AIM-KO mouse (Lane 4), microglia isolated and proliferated from the brain of WT newborn mouse (Lane 5), and microglia isolated and proliferated from the brain of AIM-KO newborn mouse (Lane 6), and the expression of AIM was analyzed by the quantitative RT-PCR method using relative expression based on the expression in the liver as 1. As a result, significant expression of AIM was not observed in the whole brain or microglia alone.

The results are shown in FIG. 3. As shown in FIG. 3, transcription of AIM mRNA was not observed in the whole brain or intracerebral microglia of the wild-type mouse.

Summarizing the results of Examples 1-3, it is considered that the AIM gene is not transcribed in the brain, and the AIM protein is blocked at the Blood-Brain Barrier (BBB) and does not migrate into the brain.

[Example 4] Introduction of AIM into the Brain and its Localization with Amyloid Plaque Under anesthesia, Alzheimer's disease model mouse 5×FAD mouse with exposed calvarial skull was fixed with a stereotactic (or stereotaxic apparatus). Recombinant mouse AIM (rAIM, SEQ ID NO: 4) (10 μg) (dissolved in 10 μL of PBS) was microinjected under a stereoscopic microscope into the hippocampal region of the right brain of 5×FAD mouse After 3 hr, the brain tissue was isolated and fixed with 4% para-form aldehyde, and frozen sections were prepared, co-stained by an immunostaining method using antibodies against AIM (green) and amyloid beta (Aβ: red), and observed with a fluorescence microscope.

Figure 4:
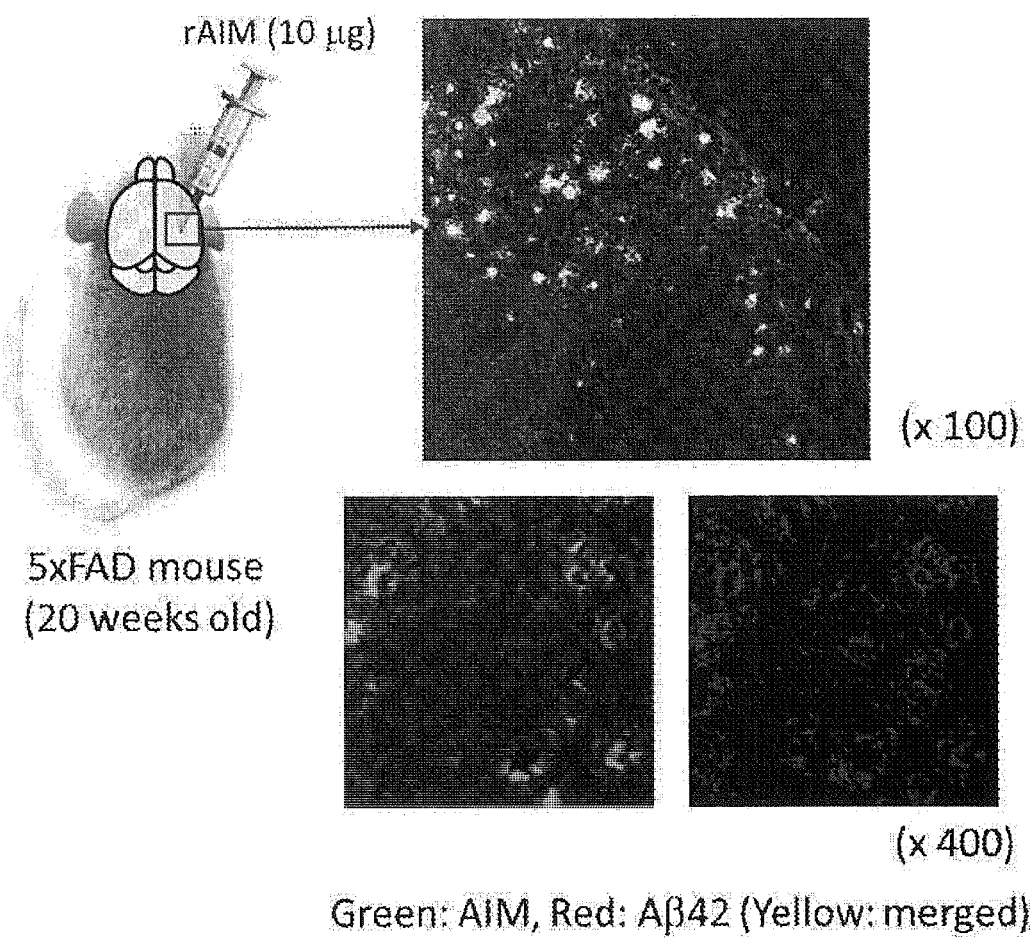
FIG. 4 Recombinant mouse AIM (rAIM) (10 μg) dissolved in PBS (dissolved in 10 μL of PBS) was microinjected into the hippocampal region of the right brain of 5×FAD mice, and after 3 hours, the brain tissue was isolated, sliced, co-stained by the immunostaining method using antibodies against AIM (green) and amyloid Aβ (red), and observed with a fluorescence microscope. Many parts of AIM and amyloid Aβ plaque were co-localized (upper Figure: yellow part due to overlapping red and green, and red and green appearing in the same part). When the other parts were highly enlarged (×400) and AIM and amyloid Aβ were photographed separately (lower Figure), the co-localization was more clearly shown.

The results are shown in FIG. 4. As shown in FIG. 4, it was shown that the recombinant AIM introduced into the hippocampal region of the 5×FAD mouse co-localized with amyloid plaque.

[Example 5] Decrease in Amyloid Plaque by Expression of AIM in the Brain

Adeno-associated virus serotype 5 (AAV-AIM) expressing mouse AIM or empty AAV5 (AAV-mock) in the same viral load was microinjected into the brain hippocampal region of 8-week-old 5×FAD mice fixed by stereotactic (or stereotaxic apparatus) (n=7-8). After 15 weeks, the brain was removed, fixed with 4% para-form aldehyde and paraffin sections were stained with anti-amyloid Aβ antibody. The % area of the amyloid Aβ-positive part (amyloid plaque) was measured using NIHimageJ software. The area of amyloid plaque to the area of the whole hippocampus was indicated in %, and compared between the mice infected with AAV-AIM and the mice infected with AAV-mock.

Figure 5:
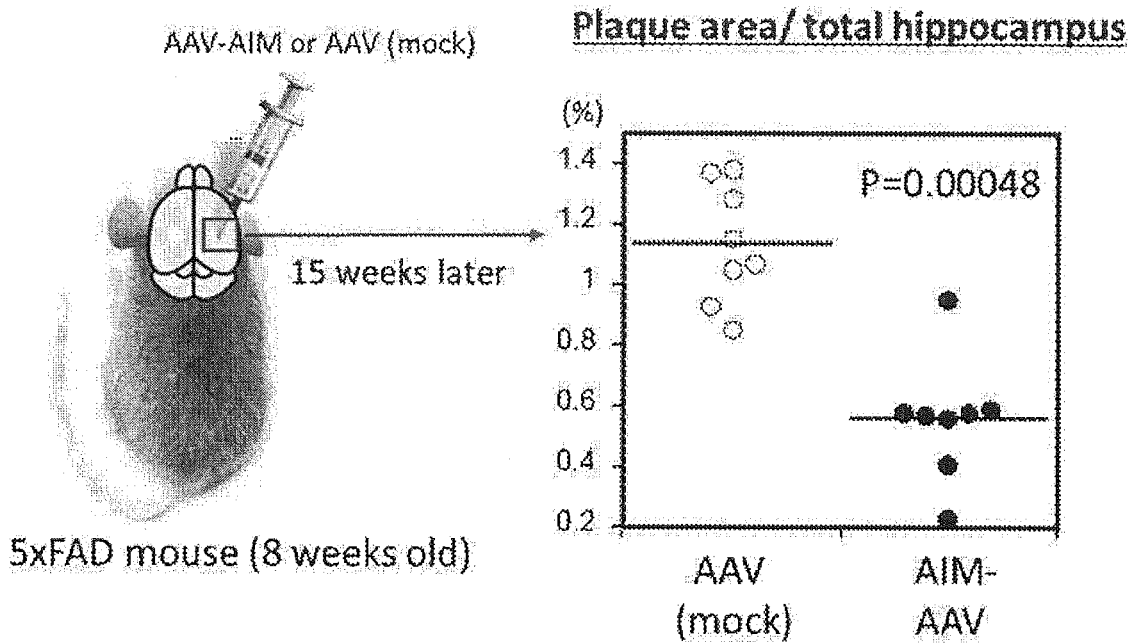
FIG. 5 Adeno-associated virus (AAV) serotype 5 (AAV5) which expresses mouse AIM or empty AAV5 (mock) was microinjected into the hippocampal region of the 8-week-old 5×FAD mice (n=7-8) with the same viral load. After 15 weeks, the brain was removed and the sections were stained with anti-amyloid Aβ antibody, and the % area of the amyloid Aβ-positive part (amyloid plaque) was compared with the total area of the hippocampus. Individuals infected with AAV expressing AIM showed a significant decrease in amyloid plaque as compared to individuals infected with mock AAV (T-test).

The results are shown in FIG. 5. As shown in FIG. 5, AIM expression adeno-associated virus infection, mock AAV infection as compared to, remarkable amyloid plaque decrease (n=7-8, P=0.00048, T-test). From the results, it was shown that delivery of AIM protein into the brain efficiently decreases intracerebral abnormal proteins.

[Example 6] Removal of Amyloid β Multimer by Binding of AIM

Ab (amyloid β) 42 peptides (Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala: SEQ ID NO: 3) labeled with Cy5 at the N-terminus were multimerized and reacted with a microglial cell population isolated and cultured from the brain of AIM-KO neonate mice, in DMEM medium+10% FBS at 37° C. for 1 hr under conditions with mouse rAIM (50 mg/mL) (+rAIM) or without it(+PBS). The cells were washed, stained with anti-F4/80 antibody, and analyzed with a flow cytometer.

Figure 6:
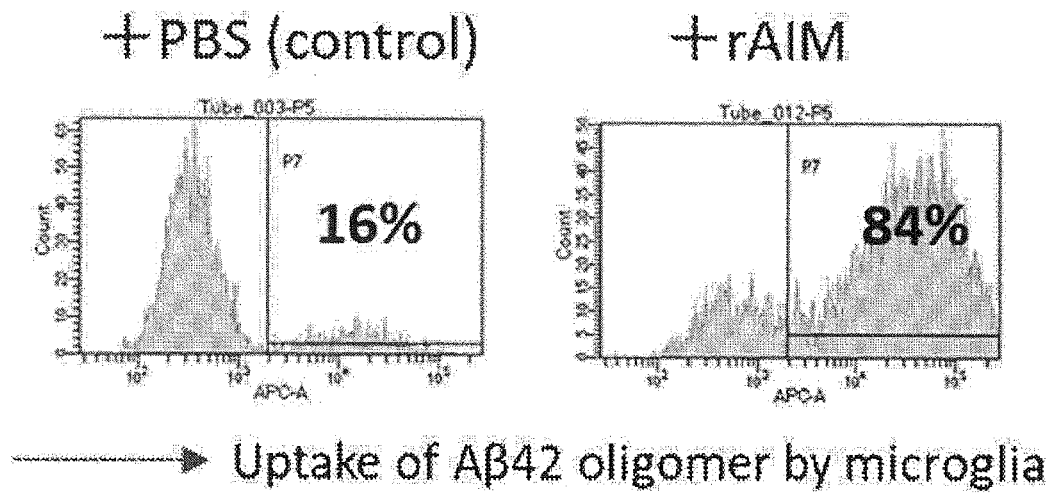
FIG. 6 Ab (amyloid β) 42 peptides labeled with Cy5 at the N-terminus were multimerized and reacted with a cell population containing microglial cells, isolated and cultured from the brain of AIM-KO neonate mice, in DMEM medium+10% FBS at 37° C. for 1 hr under conditions with rAIM (50 mg/mL) (+rAIM) or without it (+PBS). The cells were washed, stained with anti-F4/80 antibody, and analyzed with a flow cytometer. The fluorescence intensity of Cy5 in F4/80 highly positive microglia, namely, the amount of Ab42 multimer uptake was analyzed. As a result, Cy5-positive microglia remarkably (16%→84%) increased in the presence of rAIM than in the absence thereof.

The results are shown in FIG. 6. The fluorescence intensity of Cy5 in F4/80 highly positive microglia, namely, the degree of Ab42 multimer uptake was analyzed. As a result, Cy5-positive microglia remarkably (16%→84%) increased in the presence of rAIM than in the absence thereof. That is, it was shown that marking the abnormal protein, Ab42 multimer, by AIM markedly promoted the uptake of Ab42 multimer by microglia.

Though not wanting to be bound by theory, the above results are considered to mean the following mechanism. That is, generally, AIM does not exist in the brain. Thus, even when the amyloid β multimer that causes Alzheimer's disease accumulates, microglia cannot efficiently remove same. However, when AIM is delivered or expressed in the brain using some method, AIM marks amyloid β multimer as an abnormal protein. As a result, microglia can efficiently remove amyloid β multimer, thus achieving the treatment or prophylaxis of Alzheimer's disease.

[Example 7] Decrease in Aβ(Amyloid) Plaque Area by AIM Expression

Figure 9:
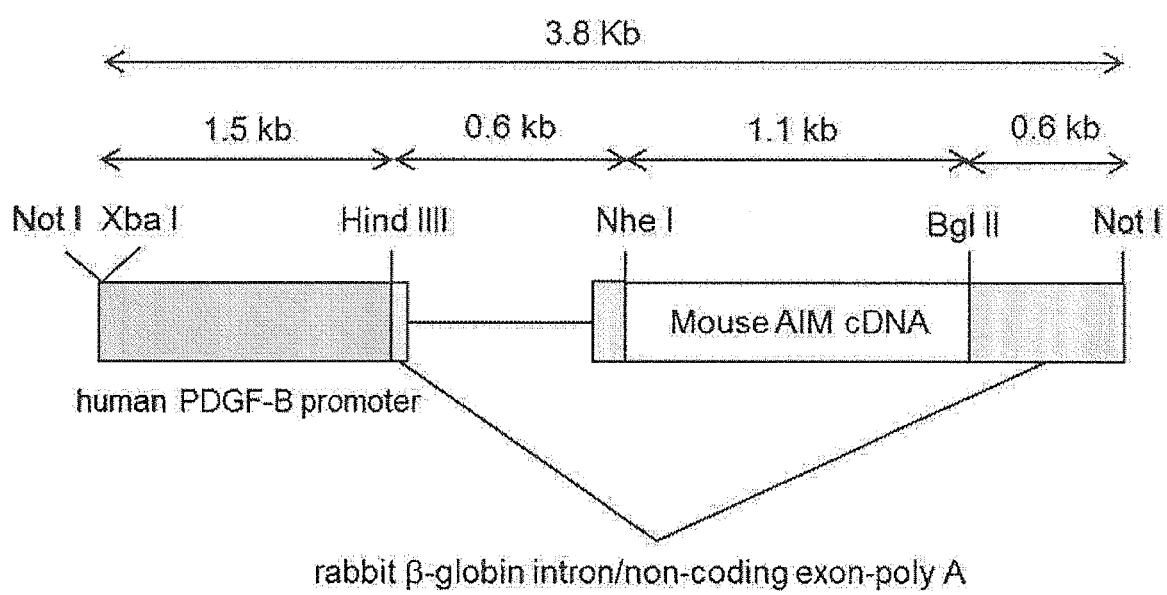
FIG. 9 A Figure showing the map of a transgene which expresses mouse AIM in a brain nerve cell under a human PDGF-B promoter. The length of each fragment is shown in Kb (kilobase).

5×FAD mouse was crossed with transgenic mouse (TG) expressing mouse AIM in brain nerve cells under human PDGF-B promoter to generate 5×FAD mouse without transgene (Non-TG) and 5×FAD mouse with transgene (TG(+)). The map of the transgene used to generate transgenic mouse (TG) expressing mouse AIM in brain nerve cell under human PDGF-B promoter is shown in FIG. 9. The human PDGF-B promoter sequence (Xba I-Hind III) (SEQ ID NO: 6) is described in detail in "PDGF B-chain in neurons of the central nervous system, posterior pituitary, and in a transgenic model. Sasahara M, Fries J W, Raines E W, Gown A M, Westrum L E, Frosch M P, Bonthron D T, Ross R, Collins T. Cell. 1991 Jan. 11; 64(1):217-227".

Figure 7:
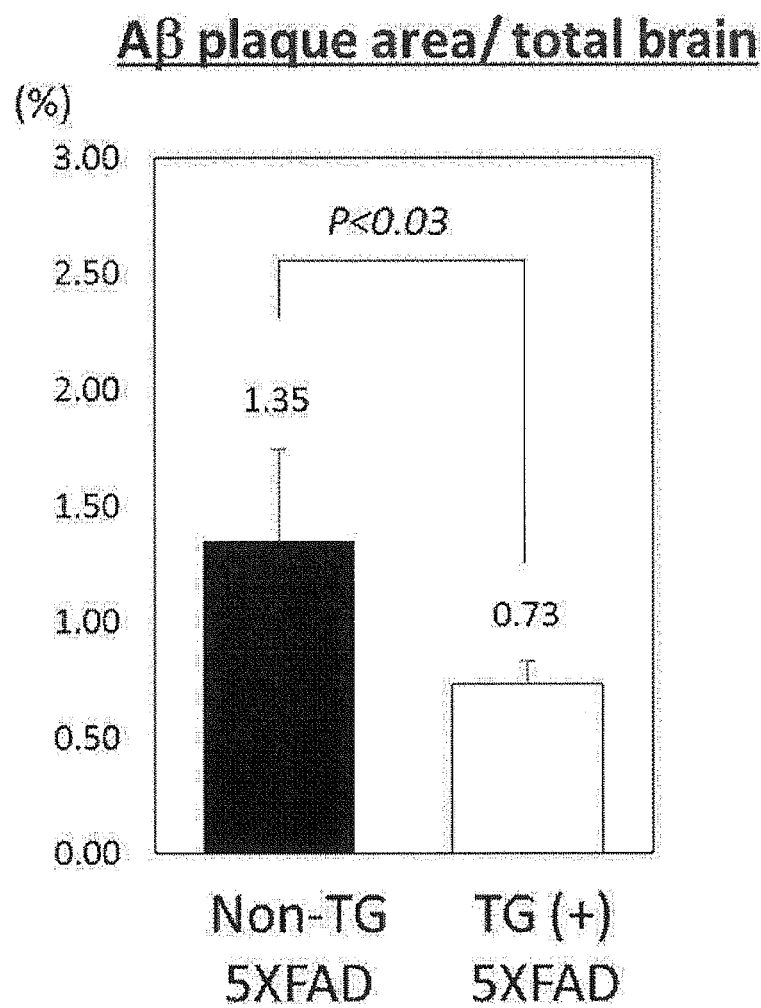
FIG. 7 A graph showing a comparison of the Aβ (amyloid) plaque area (%) in 7-week-old non-transgene (Non-TG) 5×FAD mice and TG(+) 5×FAD mice with respect to the whole brain.

At 7 weeks of age, the Aβ(amyloid) plaque area (%) to the whole brain was compared in these mice. The results thereof are shown in FIG. 7. As shown in FIG. 7, a significant decrease in the plaque was found in TG(+)5×FAD mouse (T-TEST).

[Example 8] Co-Localization of AIM and Aβ(Amyloid) Plaque in Brain Tissue

Figure 8:
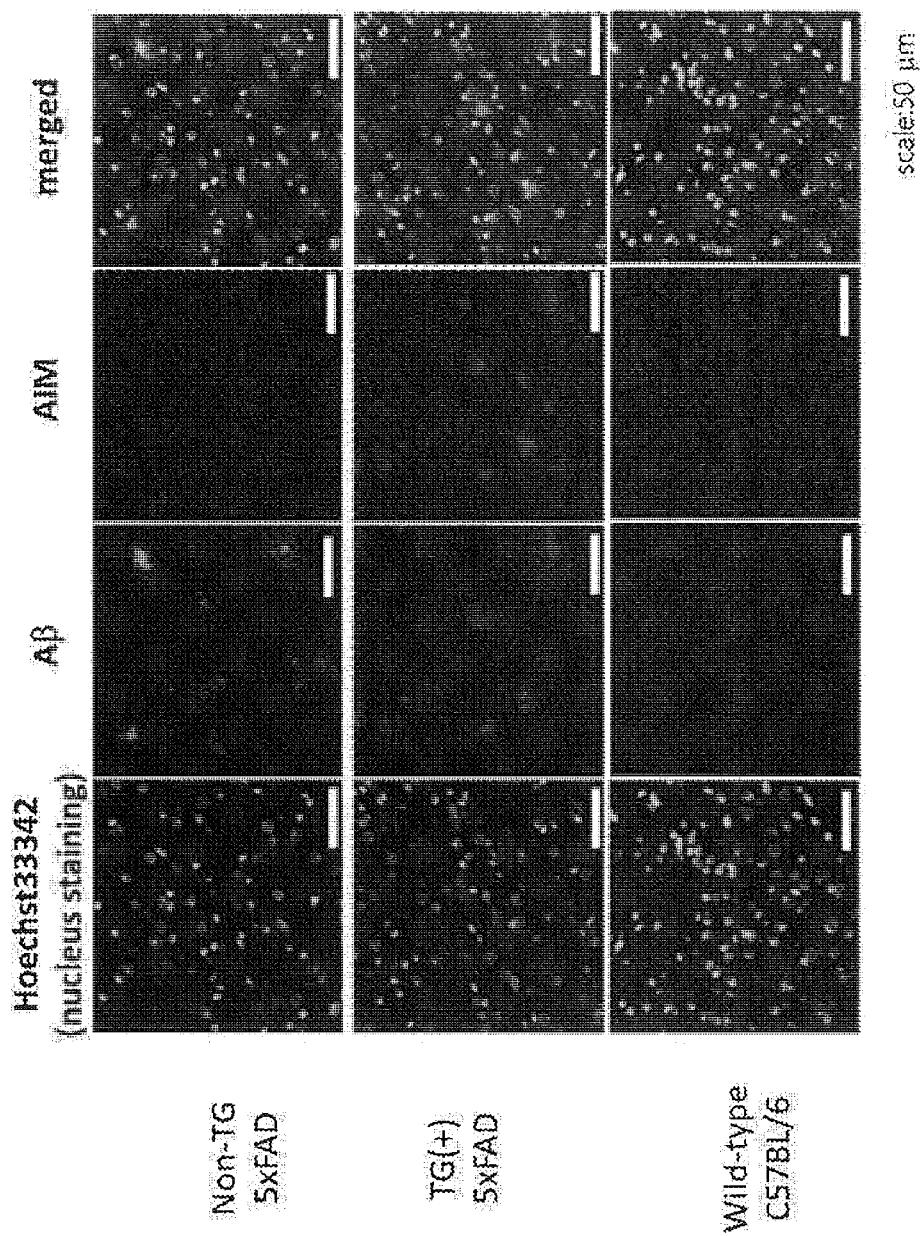
FIG. 8 A photograph showing the colocalization of AIM and Aβ plaque in the hippocampal region of 7-week-old Non-TG 5×FAD mice, TG(+) 5×FAD mice, and wild-type C57BL/6 mice.

Brain tissues were isolated from 7-week-old Non-TG 5×FAD mouse, TG(+)5×FAD mouse, and wild-type C57BL/6 mouse. Sections were prepared, co-stained by an immunostaining method using antibodies against AIM (red) and Aβ (green), and localization of these proteins was observed with a fluorescence microscope. The results are shown in FIG. 8. As shown in FIG. 8, many parts of AIM and Aβ plaque were co-localized (upper Figure: yellow part due to overlapping red and green, and red and green appearing in the same part) in TG(+)5×FAD mouse. While the photograph shows hippocampal region, such co-localization of AIM and Aβ plaque was confirmed in the whole brain.

INDUSTRIAL APPLICABILITY

The present invention is extremely useful in the medical field since it can treat and/or prevent neurodegenerative diseases including Alzheimer's disease.

This application is based on a patent application No. 2018-186759 filed in Japan (filing date: Oct. 1, 2018), the contents of which are incorporated in full herein.

The invention claimed is:

1. A method for treating a neurodegenerative disease, comprising administering Apoptosis Inhibitor of Macrophage (AIM) or a nucleic acid encoding the AIM to a subject with a neurodegenerative disease,
wherein the AIM is a human-derived AIM protein having the amino acid sequence of SEQ ID NO: 1, and
wherein the neurodegenerative disease is a disease caused by amyloid plaque in the brain,
whereby the neurodegenerative disease is treated in the subject.

2. The method according to claim 1, wherein the nucleic acid encoding AIM is incorporated in a viral vector.

3. The method according to claim 2, wherein the viral vector is a viral vector selected from the group consisting of adeno-associated virus, adenovirus, lentivirus, and Sendai virus.

4. The method according to claim 2, wherein the viral vector is an adeno-associated virus.

5. The method according to claim 4, wherein the adeno-associated virus is AAV serotype 5 (AAV5) or AAV serotype 9 (AAV9).

6. The method according to claim 1, wherein the neurodegenerative disease is selected from the group consisting of Alzheimer's disease, Parkinson's disease, Lewy body dementia, multiple system atrophy, Pick disease, corticobasal degeneration, progressive supranuclear paralysis, amyotrophic lateral sclerosis, spinobulbar muscular atrophy, Huntington's disease, spinocerebella degeneration, and dentatorubral-pallidoluysian atrophy.

7. The method according to claim 2, wherein the neurodegenerative disease is selected from the group consisting of Alzheimer's disease, Parkinson's disease, Lewy body dementia, multiple system atrophy, Pick disease, corticobasal degeneration, progressive supranuclear paralysis, amyotrophic lateral sclerosis, spinobulbar muscular atrophy, Huntington's disease, spinocerebella degeneration, and dentatorubral-pallidoluysian atrophy.

8. The method according to claim 3, wherein the neurodegenerative disease is selected from the group consisting of Alzheimer's disease, Parkinson's disease, Lewy body dementia, multiple system atrophy, Pick disease, corticobasal degeneration, progressive supranuclear paralysis, amyotrophic lateral sclerosis, spinobulbar muscular atrophy, Huntington's disease, spinocerebella degeneration, and dentatorubral-pallidoluysian atrophy.

9. The method according to claim 4, wherein the neurodegenerative disease is selected from the group consisting of Alzheimer's disease, Parkinson's disease, Lewy body dementia, multiple system atrophy, Pick disease, corticobasal degeneration, progressive supranuclear paralysis, amyotrophic lateral sclerosis, spinobulbar muscular atrophy, Huntington's disease, spinocerebella degeneration, and dentatorubral-pallidoluysian atrophy.

10. The method according to claim 5, wherein the neurodegenerative disease is selected from the group consisting of Alzheimer's disease, Parkinson's disease, Lewy body dementia, multiple system atrophy, Pick disease, corticobasal degeneration, progressive supranuclear paralysis, amyotrophic lateral sclerosis, spinobulbar muscular atrophy, Huntington's disease, spinocerebella degeneration, and dentatorubral-pallidoluysian atrophy.

* * * * *